United States Patent
Poncelet et al.

(12)

(10) Patent No.: US 6,627,208 B2
(45) Date of Patent: Sep. 30, 2003

(54) BIOCIDAL MATERIAL WITH IMPROVED ACTIVITY

(75) Inventors: Olivier Jean Poncelet, Chalon sur Saone (FR); Danielle M. Wettling, Chatenoy le Royal (FR)

(73) Assignee: Eastman Kodak Company, Rochester, NY (US)

( * ) Notice: Subject to any disclaimer, the term of this patent is extended or adjusted under 35 U.S.C. 154(b) by 87 days.

(21) Appl. No.: 09/726,941

(22) Filed: Nov. 30, 2000

(65) Prior Publication Data

US 2001/0003000 A1 Jun. 7, 2001

(30) Foreign Application Priority Data

Dec. 1, 1999 (FR) ............................................. 99 15123

(51) Int. Cl.⁷ ........................ A01N 25/00; A61K 31/425
(52) U.S. Cl. ........................................ 424/405; 514/372
(58) Field of Search ........................... 75/713; 252/106; 508/271; 424/408; 514/372

(56) References Cited

U.S. PATENT DOCUMENTS 4,822,511 A * 4/1989 Law ............................ 252/106
6,179,898 B1 * 1/2001 Poncelet et al. ............... 75/713

FOREIGN PATENT DOCUMENTS

| EP | 0 676 140 A1 | 10/1995 |
| EP | 0 937 393 A1 | 8/1999 |

* cited by examiner

*Primary Examiner*—Shelley A. Dodson
(74) *Attorney, Agent, or Firm*—Chris P. Konkol

(57) ABSTRACT

The invention relates to a biocidal material containing a specific mixture of a hydrophobic and a hydrophilic biocides, dispersed in a water-permeable matrix. The invention further concerns a method that uses the biocidal material of the invention to prevent microorganisms from growing in an aqueous solution in which such microorganisms are liable to grow.

9 Claims, 1 Drawing Sheet

BIOCIDAL MATERIAL WITH IMPROVED ACTIVITY

FIELD OF THE INVENTION

This invention concerns a biocidal material containing a specific mixture of biocides, and a method for the treatment of an aqueous solution in which micro-organisms are liable to grow, that makes use of the material of this invention.

BACKGROUND OF THE INVENTION

In industry the growth of micro-organisms in aqueous solutions is a known phenomenon that requires the use of biocides. Biocides act to inhibit the growth and (or) proliferation of micro-organisms. In particular, in the field of photography it is known that when the growth of micro-organisms goes unchecked the aqueous solutions turns into a slurry, clogging equipment, spoiling processing baths and impairing the quality of photographic images.

For environmental safety it is desirable to reduce the quantity of biocide necessary to inhibit the growth of micro-organisms. Too much biocide in effluent is unacceptable when these effluents are to be processed in wastewater treatment plants.

Many publications describe biocide mixtures. For example patent application WO 99/08530 describes a specific mixture of biocides containing a 2-methylisothiazolin-3-one compound and a 1,2-benzisothiazolin-3-one compound, compositions containing a 5-chloro-2-methylisothiazolin-3-one being excluded. This type of composition affords a synergistic biocidal effect.

Patent application EP 897 666 describes a solid biocide composition that allows the rate of release of the biocide into a solution to be reduced.

U.S. Pat. No. 4 552 752 describes a biocidal article for use in aqueous media that comprises a finely-divided water-insoluble support in which is absorbed a water-soluble biocide.

It is desirable to have a new biocidal material that allows the quantities of biocide necessary to inhibit the growth of micro-organisms to be reduced, and that remains active for several weeks.

SUMMARY OF THE INVENTION

This invention concerns a biocidal material that comprises a water-permeable matrix in which is dispersed a mixture of biocides at least one of which is a hydrophilic biocide and at least one other of which is a hydrophobic biocide. The invention concerns further a device to deliver a controlled quantity of biocide into an aqueous solution where growth of microorganisms is liable to occur.

The biocidal material of the invention displays improved efficacy. It allows a marked reduction in the quantity of biocides needed to inhibit micro-organisms. Additionally the biocidal material of the invention can be used for many weeks throughout which time it retains its biocidal activity.

DETAILED DESCRIPTION OF THE INVENTION

Figure 1:
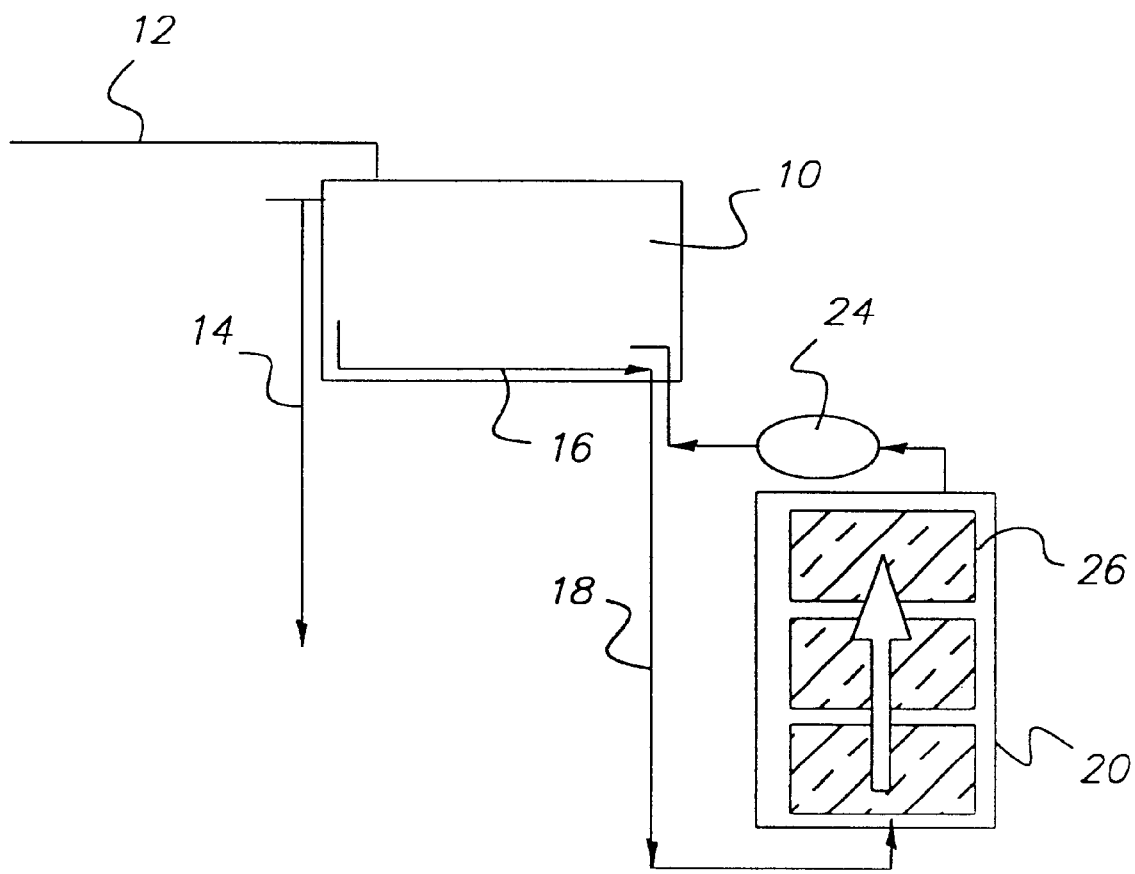
FIG. 1 represents a specific implementation of the biocidal material of the invention.

In this invention, a biocide is an organic compound that has a pesticidal, algicidal, fungicidal or bactericidal activity.

In the scope of the invention, by hydrophilic biocide is meant a biocide the water-solubility of which is greater than 1000 ppm. In contrast, a hydrophobic biocide has a water-solubility less than or equal to 1000 ppm.

Many hydrophilic and hydrophobic biocides are known in the art. From their general knowledge those skilled in the art can easily select hydrophilic or hydrophobic biocides to obtain the biocidal material of the invention.

The hydrophilic or hydrophobic biocides useful in the scope of the invention can be selected for example from among thiazole derivatives such as isothiazolones, azole derivatives, such as benzotriazoles, benzimidazoles, sulfamide-type agents, such as sulfanilamide, organo-arsenides such as 10-10'-oxybis-phenoxyarsine, benzoic acid, sorbic acid, benzalkonium quaternary ammonium salts, nitro-alcohols, quaternary ammonium salts of formula $R_5(R_6)N^+(R_7)R_8X^-$ in which $R_5$, $R_6$, $R_7$ and $R_8$ are independently aliphatic, heterocyclic or carboxylic radicals and $X^-$ is a monovalent anion, and alkylamphoacetates. These derivatives bear substituents that make the derivative either hydrophilic or hydrophobic.

Substituents that afford hydrophilic biocides are for example lower alkyl groups, preferably with 1 to 3 atoms of carbon, halogens, or a hydroxyl group.

Substituents that afford hydrophobic biocides are for example alkyl groups with more than 3 atoms of carbon, branched alkyl groups with more than 4 atoms of carbon straight- or branched-chain fluoroalkyls in which the alkyl radical contains more than 3 atoms of carbon, or perfluoro-alkyls containing a straight- or branched-chain alkyl group with more than 3 atoms of carbon.

In one embodiment, the weight ratio of the hydrophobic to the hydrophilic biocide is greater than 1.

According to a preferred embodiment, the mixture of biocides comprises at least one biocide of the hydrophilic isothiazolone type, and at least one biocide of the hydrophobic isothiazolone type.

The isothiazolones can be represented by the formula:

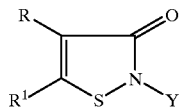

where Y is an atom of hydrogen, a substituted or unsubstituted alkyl or cycloalkyl group, a substituted or unsubstituted alkenyl group, a substituted or unsubstituted alkynyl group, and R and $R^1$ are independently an atom of hydrogen, a halogen atom or an alkyl group, or R and $R^1$ can together form a benzene moiety.

Preferably, when the biocide is a hydrophilic biocide, Y is a methyl or ethyl group, and R and $R^1$ are chloride or a methyl or ethyl group. When the biocide is a hydrophobic biocide, Y is for example an octyl group, and R and $R^1$ are alkyl groups with more than 3 atoms of carbon.

For example, hydrophilic isothiazolones can be 1,2-benzisothiazolin-3-one, 2-methyl-4-isothiazolin-3-one, or 5-chloro-2-methyl-4-isothiazolin-3-one.

For example, hydrophobic isothiazolones can be 2-octyl-4-isothiazolin-3-one, or 4,5-dichloro-2-N-octyl-4-isothiazolin-3-one.

According to a preferred embodiment, the biocidal material of the invention contains at least 50% by weight of hydrophobic biocides, calculated relative to the total quantity of biocides.

In the scope of the invention, the mixture comprising the mixture of hydrophilic and hydrophobic biocide is dispersed in a water-permeable matrix. In the scope of the invention the useful mixture of biocides does not bond covalently with this matrix, so that the biocides do not remain trapped in the matrix.

Preferably, this matrix takes the form of an aqueous gel. A gel is a three-dimensional structure that contains a solvent trapped in the structure, and that has infinite viscosity. In a specific embodiment of the invention the matrix is an aqueous gel with an inorganic three-dimensional structure and with water as the solvent.

The matrix that is useful in the scope of the invention, when it is in gel form, can be obtained by gelling an aqueous solution containing an inorganic polymer or a precursor of such a polymer and the mixture of biocides. The gelling is generally achieved by means of an ionic additive. This additive is selected so that it does not react with the mixture of biocides.

According to a preferred embodiment, the inorganic matrix is an aqueous aluminosilicate gel, preferably imogolite. Imogolite is a crystallized aluminosilicate polymer. The imogolite gel can be obtained in the form of a fibrous aluminosilicate polymer of formula $Al_xSi_yO_z$ (x:y ranging from 1 to 3, and z ranging from 2 to 6). A procedure for obtaining such a gel is described in Patent Application FR 9802364.

The matrix can comprise a mixture of fibrous aluminosilicate polymer and non-fibrous inorganic particles that are chemically inert and do not react with the solution in which the gel is placed, such as particles of alumina, silica, aluminosilicate or hydrotalcites.

For the biocidal material of the invention to act, the aqueous solution to be treated, for example water, must flow through it. The biocidal material can be used directly or placed in a container that is permeable to the solution to be treated. In practice the biocidal material can be placed in a porous material of pore size in the range 1 nm to 50 microns. The porous material can for example be a dialysis tube, made for example of chemically inert cellulose, or a closed bag made of filter paper or a non-woven material. The biocidal material can in certain cases be prepared directly in the porous material.

The quantity of biocides that can be dispersed in the matrix varies widely according to the mixture of biocides or the solution to be treated. When imogolite in the form of an aqueous gel is used, the molar ratio of the matrix to the mixture of biocides can be in the range 10:1 to 1:200.

The biocidal material of the invention can be used in any application in which the bacteriological quality of water has to be controlled.

For example, the biocidal material of the invention can be used advantageously in a photographic processing machine. Conventionally, such processing machines comprise a developing bath, a bleaching bath, a fixing bath and one or more washing baths. The biocidal material of the invention can be used in any of these baths, preferably for the treatment of a washing bath.

In the field of traditional medical imaging, it is desirable to reduce bacterial proliferation as much as possible. In radiographic film processing methods the presence of bacteria causes defects on the developed films. Such defects can lead to false diagnosis. Also, the proliferation of bacteria causes a biofilm to form on the walls of the processing tanks and on the film drive rollers and sprockets, so that the machines have to be shut down for cleaning.

FIG. 1 shows an embodiment of the invention for the treatment of an aqueous solution with the biocidal material of the invention. On this figure, a tank 10, which can be a processing tank in a photographic processing machine, is supplied with water through piping 12. This tank 10 is equipped with an overflow 14 to keep the volume of solution contained in tank 10 constant. The tank is also equipped with an outlet 16 connected by piping 18 to a processing device 20 containing the biocidal material of the invention. The processing unit 20 is connected to a pump 24 that sends the processed solution back to tank 10. The treatment unit 20 can comprise several elements 26. In the specific embodiment depicted in FIG. 1, the treatment unit 20 comprises three elements 26.

In a specific embodiment, at least two elements contain the biocidal material. The third element can contain a material of a different nature, for example a material to trap compounds that are to be eliminated from the solution. For example, the third element can contain a material that can trap the silver contained in the solution to be processed.

In a specific embodiment, each element can be replaced independently of the others.

The solution to be processed that is liable to contain bacteria flows through the processing unit 20, which contains at least one element containing the biocidal material of the invention. While it flows through the biocidal material the solution takes up biocide. This solution now containing biocide is then pumped back to the processing tank 10. It is thus possible to curtail bacterial growth in the solution.

EXAMPLE 1

Preparation of an Aqueous Solution of Imogolite

To 1,000 ml of de-ionized water was added 16.7 mmoles of tetraethylorthosilicate $Si(OR)_4$. The reaction mixture was stirred at ambient temperature for one hour and this solution was then added to 31.2 mmoles of $AlCl_3.6H_2O$ dissolved in 1,000 ml of pure water. The mixture was stirred for 20 minutes and its pH adjusted to 4.5 with 1M NaOH. The solution became turbid. When the solution became clear again, 1M NaOH was added to bring the pH to 6.8. A white gel was obtained, which was spun for 20 minutes at 2,000 r.p.m. The gel was collected and redissolved in 5 ml of a mixture containing 1M HCl and 2M acetic acid. This volume was made up to 2 liters with water. The resulting solution contained 30 mmoles of Al, 16.6 mmoles of Si, 5 mmoles of HCl and 10 mmoles of acetic acid. This solution was stored at 5° C.

This solution was then diluted with deionized water to obtain an Al concentration of 10 mmoles/l. The diluted solution was then heated for five days at 96° C. and filtered through an ultrafiltration membrane with a separation power of 10,000 Daltons (membrane manufactured by AMICON). A clear solution was obtained containing Al and Si in an Al:Si ratio of 1.8.

EXAMPLE 2

(Invention)

Preparation of the Biocidal Material

A gel containing Kathon 287T®, a hydrophobic biocide marketed by Rohm & Haas, was prepared using the following procedure.

1 kg of pure Kathon 287T® was dissolved with vigorous stirring in 1 liter of methanol 50° C.

This homogeneous solution was added to 10 liters of a 2 g/l solution of imogolite prepared as described in example 1. The addition was carried out slowly at 50° C. with rapid mechanical stirring. The mixture was then allowed to cool with stirring. When the temperature reached 25° C. N ammonia was added (210 ml) to obtain a gel comprising imogolite as an aqueous gel in which the hydrophobic Kathon 287T® was dispersed.

A gel containing Kathon LX®, a mixture of hydrophilic biocides totally soluble in water, marketed by Rohm & Haas, was prepared using the following procedure.

100 ml of Kathon LX® were mixed with 50 ml of methanol. This solution was added to 5 liters of a 2 g/l solution of imogolite. The addition of the solution of Kathon LX® was carried out with mechanical stirring at ambient temperature. Ammonia was then added (16 ml). The stirring was stopped as soon as the mass of gel appeared. After a few minutes a compact gel was obtained.

The biocidal material of the invention was obtained by mixing the gel prepared above in which the Kathon 287T® was dispersed (solubility in water 5 mg/l) with the gel prepared above in which the Kathon LX® was dispersed.

Kathon 287T®

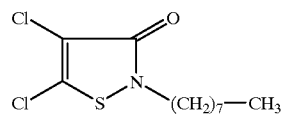

Kathon LX®: Aqueous solution containing 13.7% by weight of isothiazolones of formula:

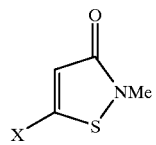

X = Cl, H where the chloroisothiazolone:isothiazolone ratio is 3:1.

EXAMPLE 3

In a dialysis bag (cellulose ester, Spectra Por$^R$, MWCO= 500, diameter 10 mm, vol/length 0.81 ml/cm-Roth) was placed 1 g of Kathon 287T® and 1 ml of the solution of Kathon LX® with 2.5 mg of active substance.

In a second dialysis bag (Spectra Por$^R$, MWCO=3,500, diameter 34 mm, vol/length 9.3 ml/cm-Roth) was placed a mixture of gels prepared using the procedure described in example 2 from 1 ml of the solution of Kathon LX® (2.5 mg active material) added to 2 ml of imogolite (3 g/l), the gel being obtained by addition of one drop of ammonia and from 1 g of Kathon 287T® (1 g active substance) dissolved in 2 ml of hot methanol (50° C.) to which had been added 16 ml of a solution of imogolite (2 g/l).

Each bag was dipped in 100 ml of osmosed water. The osmosed water was replenished at regular time intervals. The recovered water was analyzed by UV-visible spectrophotometry. The optical density measured was characteristic of the quantity of biocide present in the osmosed water. A wavelength of 273 nm is characteristic of Kathon LX®, a wavelength of 278 nm is characteristic of Kathon 287T®, and an intermediate wavelength is characteristic of a mixture of Kathon LX® and Kathon 287T®.

The results are given in Table 1 below.

TABLE 1

| | Optical density measured (wavelength) | |
|---|---|---|
| Time in days | Kathon LX ® and Kathon 287T ® | Imogolite containing Kathon LX ® and Kathon 287T ® |
| 1 | 1.3636 (273 nm) | 0.8334 (273 nm) |
| 5 | 0.1689 (276 nm) | 0.3753 (273 nm) |
| 7 | 0.0871 (278 nm) | 0.1832 (277 nm) |
| 11 | 0.0902 (278–279 nm) | 0.1581 (278 nm) |
| 25 | No measurements | 0.1607 (278 nm) |
| 39 | 0.1275 (278 nm) | 0.1508 (278 nm) |

After one day most of the Kathon LX® contained in the bag without imogolite had diffused into the osmosed water. The biocide contained in the gel diffused more slowly.

After five days, the optical density was greater with the gel containing the mixture of biocides.

These examples show that imogolite delays the diffusion of the biocides, thereby affording a biocidal material of prolonged efficacy.

EXAMPLE 4

In this example the following biocides were prepared

Ex. 4.1: gel containing only Kathon LX®. The gel was obtained as from 1 ml of Kathon LX® (i.e., 2.5 mg of active substance), 19 ml of imogolite (2 g/l) and ammonia.

Ex. 4.2: gel containing only Kordek®, a hydrophilic biocide completely soluble in water, marketed by Rohm & Haas. The gel is obtained from 5.1 mg of Kordek® (active substance 2.5 mg), 19 ml of imogolite (2 g/l) and ammonia.

Ex. 4.3: gel containing only Kathon 287T®. The gel is obtained from 1 g of Kathon 287T® dissolved in 2 ml of hot methanol (50° C.), 17 ml of imogolite (2 g/l) and ammonia.

Ex. 4.4: gel containing a mixture of Kathon LX® and Kathon 287T®. The biocidal material is obtained by mixing the two gels prepared using the procedure described in example 2. A first gel was prepared from 1 g of Kathon 287T® dissolved in 2 ml of hot methanol (50° C.), to which was added 16 ml of imogolite (2 g/l) and ammonia. The second gel was obtained from 1 ml of Kathon LX®, 2 ml of imogolite (3 g/l) and ammonia to cause the solution to gel.

Ex. 4.5: gel containing a mixture of Kordek® and Kathon 287T® obtained using the procedure described in example 4.4 from 5.1 mg of Kordek® and 1 g of Kathon 287T®.

These different gels were placed in dialysis bags, which were placed in conical flasks containing 100 ml of osmosed water. After different times this water was recovered and analyzed to monitor the diffusion of the biocides. The water was each time replenished.

The results are given in Tables 2, 3 and 4.

TABLE 2

| Time in days | Ex. 4.4: Imogolite/Kathons LX ® + 278T ® OD (wavelength) | Ex. 4.1: Imogolite/Kathon LX ® OD (wavelength) |
|---|---|---|
| 1 | 0.8334 (273 nm) | 0.8182 (273 nm) |
| 5 | 0.3753 (273 nm) | 0.1622 (273 nm) |
| 7 | 0.1832 (277 nm) | 0.0334 (273 nm) |
| 11 | 0.1581 (278 nm) | 0.0111 (273 nm) |

TABLE 2-continued

| Time in days | Ex. 4.4: Imogolite/Kathons LX ® + 278T ® OD (wavelength) | Ex. 4.1: Imogolite/Kathon LX ® OD (wavelength) |
|---|---|---|
| 25 | 0.1607 (278 nm) | 0 |
| 39 | 0.1508 (278 nm) | 0 |

TABLE 3

| Time in days | Ex. 4.5: Imogolite/ Kordek ® + Kathon 278T ® OD (wavelength) | Ex. 4.2: Imogolite/Kordek ® OD (wavelength) |
|---|---|---|
| 1 | 1.4338 (273 nm) | 1.3240 (273 nm) |
| 3 | 0.5013 (274 nm) | 0.4629 (273 nm) |
| 6 | 0.2409 (276–277 nm) | 0.1185 (273 nm) |
| 10 | 0.1838 (278 nm) | 0.0289 (273 nm) |
| 14 | 0.1469 (278 nm) | 0.0099 (273 nm) |
| 17 | 0.1288 (278 nm) | 0.0024 (273 nm) |
| 27 | 0.1408 (278 nm) | 0.0015 (273 nm) |

TABLE 4

| | Ex. 4.3: Kathon 287T ® | |
|---|---|---|
| Test C | OD (278 nm) | Concentration |
| 1 day | 0.0638 | 2.8 mg/l |
| 3 days | 0.1369 | 5.0 mg/l |

The results show that after several days the optical density of the water analyzed by UV-visible spectrophotometry in the case of the gel containing a single biocide fell rapidly.

The optical density of the water in contact with the gel containing the two biocides also fell, but it always remained greater than the optical density of the water in contact with the gel containing a single biocide. In addition the presence of biocide was detected for a longer time. The medium remained clean longer.

The results observed when Kathon LX® was replaced by Kordek® were similar.

Table 4 shows that with a gel containing only Kathon 287T® the concentration of Kathon 287T® reached a maximum after three days (limit of solubility 5 mg/l), whereas with a mixture of Kathon LX® +Kathon 287T® or Kordek+ Kathon 287T®, the quantity of Kathon 287T® in the water became predominant only after 10 days.

EXAMPLE 5

In this example the following biocidal materials were placed in dialysis bags.

Mat. 5.1: 20 g of a 2 g/l imogolite gel prepared using the procedure described in example 1, gelling being caused by addition of ammonia.

Mat. 5.2: 10 ml of Kathon LX® (active substance 1.4 mg) and 20 g of imogolite (2 g/l) prepared using the procedure described in example 1, gelling being caused by addition of $NH_4OH$.

Mat. 5.3: 1.2 g of Kathon 287T® (active substance 1.2 g), and 20 g of imogolite (2 g/l).

Mat. 5.4: 1.2 g of Kathon 287T® (active substance 1.2 g) and 10 ml of Kathon LX® (active substance 1.4 g) and 20 g of imogolite (2 g/l).

These gels were placed in a cell containing $10^9$ cfu of *Pseudomonas aeruginosa* NCIMB 10421 bacteria. After 168 hours the water was replenished with water containing $10^9$ cfu of bacteria.

The results are given in the Table below.

| Time (hours) | Mat. 5.1 | Mat. 5.2 | Mat 5.3 | Mat 5.4 |
|---|---|---|---|---|
| 0 | $1.83^E + 09$ | $1.83^E + 09$ | $2.00^E + 09$ | $1.50^E + 09$ |
| 1 | $2.50^E + 09$ | $6.33^E + 08$ | $8.17^E + 08$ | $5.67^E + 08$ |
| 3 | $1.52^E + 09$ | $1.95^E + 06$ | $1.67^E + 08$ | 1 |
| 5 | $1.35^E + 09$ | 1 | 1 | 1 |
| 7 | $1.72^E + 09$ | 1 | 1 | 1 |
| 24 | $1.37^E + 09$ | 1 | 1 | 1 |
| 31 | $1.53^E + 09$ | 1 | 1 | 1 |
| 48 | $1.27^E + 09$ | 1 | 1 | 1 |
| 144 | $6.83^E + 09$ | 1 | 1 | 1 |
| 168 | $1.67^E + 09$ | $1.50^E + 09$ | $1.67^E + 09$ | $2.17^E + 09$ |
| 169 | $1.67^E + 09$ | $1.57^E + 09$ | $4.17^E + 08$ | $6.00^E + 08$ |
| 171 | $1.65^E + 09$ | $1.17^E + 09$ | $2.67^E + 07$ | $2.17^E + 07$ |
| 173 | $2.93^E + 09$ | $1.00^E + 09$ | $7.50^E + 04$ | 1 |
| 175 | $1.62^E + 09$ | $1.38^E + 09$ | $1.67^E + 02$ | 1 |
| 192 | $1.48^E + 09$ | $5.17^E + 08$ | 1 | 1 |
| 199 | $1.78^E + 09$ | $9.50^E + 07$ | 1 | 1 |
| 216 | $1.45^E + 09$ | $2.67^E + 07$ | 1 | 1 |

Mat. 5.1: Control-level of bacteria unchanged.
Mat. 5.2: After one week the biocidal material was no longer bactericidal.
Mat. 5.3: When the medium was changed (168 h) the biocidal material became active more slowly.
Mat. 5.4: The biocidal material rapidly became active (3 h), and remained active even after changing the medium (168 h).

These results show the synergistic effects of the material on a population of specific bacteria.

The invention has been described in detail with particular reference to certain preferred embodiments thereof, but it will be understood that variations and modifications can be effected within the spirit and scope of the invention.

What we claimed:

1. A biocidal material consisting of a water-permeable matrix in which is dispersed a mixture of biocides at least one of which is a hydrophilic biocide and at least one other of which is a hydrophobic biocide.

2. The biocidal material of claim 1, wherein said hydrophilic biocide and said hydrophobic biocide are present in quantities such that the weight ratio of the hydrophobic biocide to the hydrophilic biocide is greater than one.

3. The biocidal material of claim 1, wherein said biocides are selected from the class consisting of isothiazolones.

4. The material of claim 1, wherein said water-permeable matrix is an inorganic matrix in gel form.

5. The biocidal material of claim 4, wherein said inorganic water-permeable matrix in gel form is a gel comprising imogolite-type aluminosilicate and at least 50% water by weight.

6. A device to deliver a controlled quantity of biocide into an aqueous solution in which growth of microorganisms is liable to occur, comprising a support that is permeable to the aqueous solution in which is placed the biocidal material of claim 1.

7. A method to eliminate microorganisms from an aqueous solution in which said microorganisms are liable to grow, wherein said aqueous solution is placed in contact with the biocidal material of claim 1.

8. The method of claim 7 for eliminating microorganisms from photographic processing baths.

9. The method of claim 7 for eliminating microorganisms from a photographic washing bath.

* * * * *